(12) United States Patent
Breslin

(10) Patent No.: US 11,351,351 B2
(45) Date of Patent: Jun. 7, 2022

(54) DEVICE FOR SANITIZING INJECTION PORTS AND METHODS OF USE

(71) Applicant: Thomas R. Breslin, Hampton, NH (US)

(72) Inventor: Thomas R. Breslin, Hampton, NH (US)

(73) Assignee: Perigean Medical, LLC, Hampton, NH (US)

( * ) Notice: Subject to any disclaimer, the term of this patent is extended or adjusted under 35 U.S.C. 154(b) by 342 days.

(21) Appl. No.: 16/239,659

(22) Filed: Jan. 4, 2019

(65) Prior Publication Data

US 2019/0209826 A1 Jul. 11, 2019

Related U.S. Application Data

(60) Provisional application No. 62/615,479, filed on Jan. 10, 2018.

(51) Int. Cl.
| | | |
|---|---|---|
| *A61M 39/16* | (2006.01) | |
| *A61M 5/30* | (2006.01) | |
| *A61L 2/16* | (2006.01) | |
| *A61B 90/70* | (2016.01) | |
| *A61M 39/20* | (2006.01) | |
| *A61M 39/10* | (2006.01) | |
| *A61M 39/02* | (2006.01) | |

(52) U.S. Cl.
CPC ............. *A61M 39/16* (2013.01); *A61B 90/70* (2016.02); *A61L 2/16* (2013.01); *A61M 5/30* (2013.01); *A61M 39/20* (2013.01); *A61M 39/0208* (2013.01); *A61M 2039/1077* (2013.01)

(58) Field of Classification Search
CPC . A61L 2/16; A61M 39/16; A61M 5/30; A61B 90/70

See application file for complete search history.

(56) References Cited

U.S. PATENT DOCUMENTS

| | | | |
|---|---|---|---|
| 8,628,501 B2 * | 1/2014 | Hadden | A61M 39/16 604/199 |
| 8,845,593 B2 * | 9/2014 | Anderson | A61M 39/162 604/187 |
| 10,166,339 B2 * | 1/2019 | Solomon | A61M 5/30 |
| 2011/0054440 A1 * | 3/2011 | Lewis | A61M 39/20 604/506 |
| 2012/0039764 A1 * | 2/2012 | Solomon | A61L 2/23 422/292 |

* cited by examiner

*Primary Examiner* — Sean E Conley
(74) *Attorney, Agent, or Firm* — Pierce Atwood LLP; Kevin M. Farrell; Christopher A. Baxter

(57) ABSTRACT

Devices and methods for sanitizing injection ports on intravenous, intramuscular and subcutaneous injection ports.

19 Claims, 5 Drawing Sheets

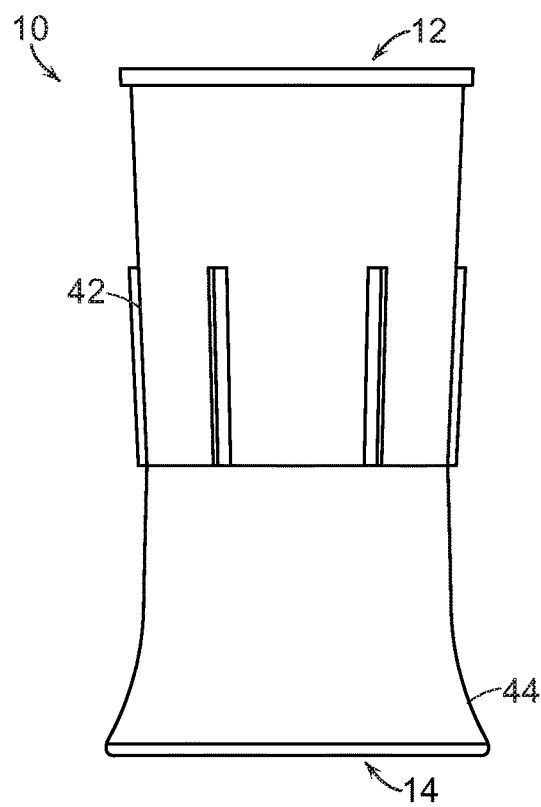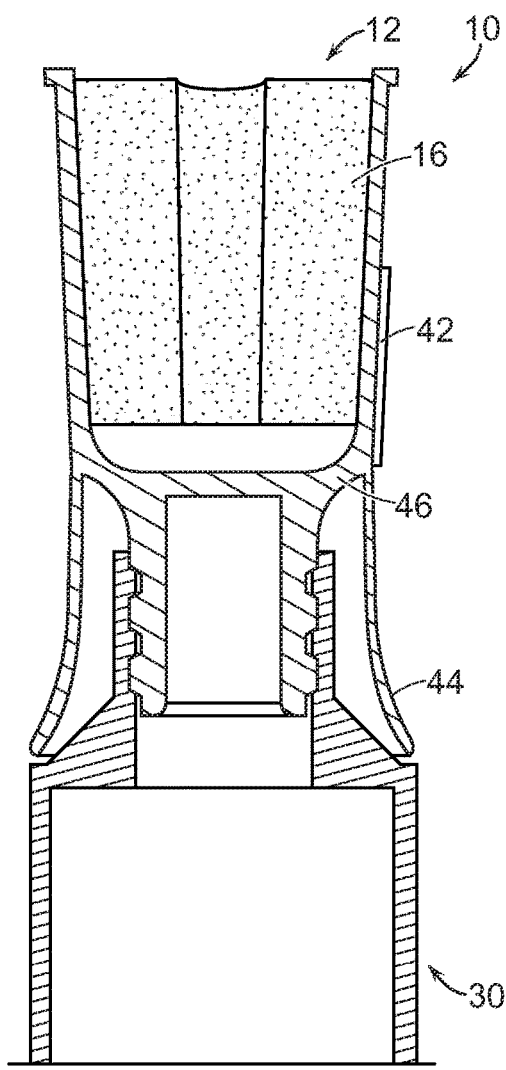

DEVICE FOR SANITIZING INJECTION PORTS AND METHODS OF USE

BACKGROUND

Preventing bloodstream infections is critical in patient care, especially when performing intravenous administration of agents and/or blood draws. Bloodstream infections are referred to as Central Line Associated Bloodstream Infections (CLABSI).

Central lines are used in approximately 48% of all intensive care (ICU) patients and are frequently used in emergency ward and general admittance patients. Central lines are intravenous lines that, once positioned in a patient, are reused usually for the duration of the patient's stay at the hospital or other healthcare facility. ICU patients may have their central line accessed as many as 20 times in a day. It is recognized in the field that CLABSI are a significant cause of morbidity and mortality in hospitalized patients. It is estimated that between 500 and 4,000 patients in the United States die annually due to CLABSI. The source of patient infection can be from contamination of the device prior to insertion, organisms found on the patient's skin, contaminated infusate and, frequently, contamination of the catheter hub. Interventions geared towards daily maintenance and routine sanitation of central lines is recognized as critical to preventing CLABSI.

Compliance with standard protocols implemented to reduce CLABSI has been shown to be the best method of reducing CLABSI. These protocols include hand washing by the practitioner, sanitation of the patient's skin, sanitation and/or careful handling of the insertion device (i.e., injection device) prior to use and sanitation of the catheter hub prior to each use. The sanitation of the catheter hub is often referred to as "Scrub the Hub."

Current methods and devices for the sanitation of the catheter hub, although generally effective, are cumbersome and, therefore, may not be practiced with the fidelity needed to ensure patient health and safety. For example, the current "gold standard" is to swab the catheter hub with an alcohol prep pad. This requires the practitioner to obtain the prep pad, open the prep pad, sanitize the catheter hub with small piece of material saturated in sanitation fluid, the practice of which requires attention to detail even during the most stressful and time limited of medical situations, and dispose of the waste materials. Devices other than prep pads are available. These devices typically have a material saturated with sanitizing fluid in a holder. However, they do little to reduce the cumbersomeness of the Scrub the Hub procedure since the devices still have to be obtained, opened and manipulated. What is needed in the art are new devices and methods for the sanitation of the catheter hub that help to ensure compliance with CLABSI preventative measures.

SUMMARY OF THE INVENTION

The present invention helps to solve these problems associated with prior art Scrub the Hub devices and methods. The present invention is directed towards a device that can be packaged integrally with an injection device, such as, for example, a syringe or catheter tubing or device for the withdrawal of fluids, e.g., blood, amniotic fluid, interstitial fluid, etc. In this regard, the device of the present invention is attached to the injection device prior to or during packaging of the injection device. The device of the present invention can be attached to the injection device at the injection end of the device. In this regard, for example, the device of the present invention may be positioned, prior to packaging, at the end of a syringe, catheter tube or other device that will couple with an injection or withdrawal port.

The device of the present invention is designed to securely fit the injection device by having a fitting compatible with the injection device. By having the sanitizing device prepackaged and attached to the injection device, the user is never without an injection port sanitizing device, critical time is saved by the user by not having to locate and open an independent sanitizing device, and sanitizing an injection port becomes integral with opening the injection device since the motions used to open and use an injection device are not disrupted to the extent they are when using an independent sanitizing device. Thus, the device and methods of the present invention will satisfy the need in the art with regard to ensuring compliance with CLABSI preventative measures and reducing CLABSI-caused patient morbidity and mortality.

Thus, the present invention contemplates a method for sanitizing a medical injection port for coupling to an injection device, the method comprising: providing, a sanitizing device removably coupled to the injection device, said sanitizing device comprising: a closed first end having a fitting suitable for coupling to the injection device and a second end comprising a recess containing an absorbent material substantially saturated with a sanitizing agent, the second end sealed with a removable seal; removing the seal from the second end of the sanitizing device; inserting the injection port into the recess of the sanitizing device such that the absorbent material substantially saturated with a sanitizing agent contacts the injection port; wherein the sanitizing device is contacted with the medical injection port for a length of time such that the injection port is sanitized; removing the sanitizing device from the medical injection port and the injection device and coupling the injection port to the injection device.

The present invention further contemplates that the removable seal is substantially resistant to moisture permeability.

The present invention further contemplates that the sanitizing agent is selected from the group consisting of isopropyl alcohol and chlorhexidine or other suitable sanitizing agent known to one or ordinary skill in the art.

The present invention further contemplates that the sanitizing agent is isopropyl alcohol at a concentration of approximately 65% to 75%.

The present invention further contemplates that the absorbent material is selected from a group consisting of open cell foam, woven material and non-woven material.

The present invention further contemplates that the injection port is contacted with the sanitizing device for a length of time selected from the group consisting of for at least five seconds, at least twenty seconds and at least sixty seconds.

The present invention further contemplates that the injection device is selected from a syringe or catheter port.

The present invention further contemplates that the medical injection port is suitable for injection sites selected from the group consisting of intravenous, intramuscular and subcutaneous injection sites.

The present invention also contemplates a device for sanitizing an medical injection port, the device comprising: a sanitizing device removably coupled to an injection device, said sanitizing device comprising: a closed first end having a fitting suitable for coupling to the injection device and a second end comprising a recess containing an absorbent material substantially saturated with a sanitizing agent, the second end sealed with a removable seal.

The present invention further contemplates that the removable seal is substantially resistant to moisture permeability.

The present invention further contemplates that the sanitizing agent is selected from the group consisting of isopropyl alcohol and chlorhexidine or other suitable sanitizing agent known to one or ordinary skill in the art.

The present invention further contemplates that the sanitizing agent is isopropyl alcohol at a concentration of approximately 65% to 75%.

The present invention further contemplates that the absorbent material is selected from a group consisting of open cell foam, woven material and non-woven material.

The present invention further contemplates that the injection device is a syringe or catheter port.

The present invention further contemplates a device for sanitizing an medical injection port, said device comprising: a sanitizing device suitable for being removably coupled to an injection device, said sanitizing device comprising: a closed first end having a fitting suitable for coupling to the injection device and a second end comprising a recess containing an absorbent material substantially saturated with a sanitizing agent, the second end sealed with a removable seal.

The present invention further contemplates that the removable seal is substantially resistant to moisture permeability.

The present invention further contemplates that the sanitizing agent is selected from the group consisting of isopropyl alcohol and chlorhexidine.

The present invention further contemplates that the sanitizing agent is isopropyl alcohol at a concentration of approximately 65% to 75%.

The present invention further contemplates that the absorbent material is selected from a group consisting of open cell foam, woven material and non-woven material.

BRIEF DESCRIPTION OF THE FIGURES

FIG. 4 shows an alternate design of the sanitization device of the present invention.

FIG. 5 shows a cross-sectional view of the alternate design of the sanitization device of the present invention attached to an injection or withdrawal device.

DETAILED DESCRIPTION OF THE INVENTION

Figure 1A:
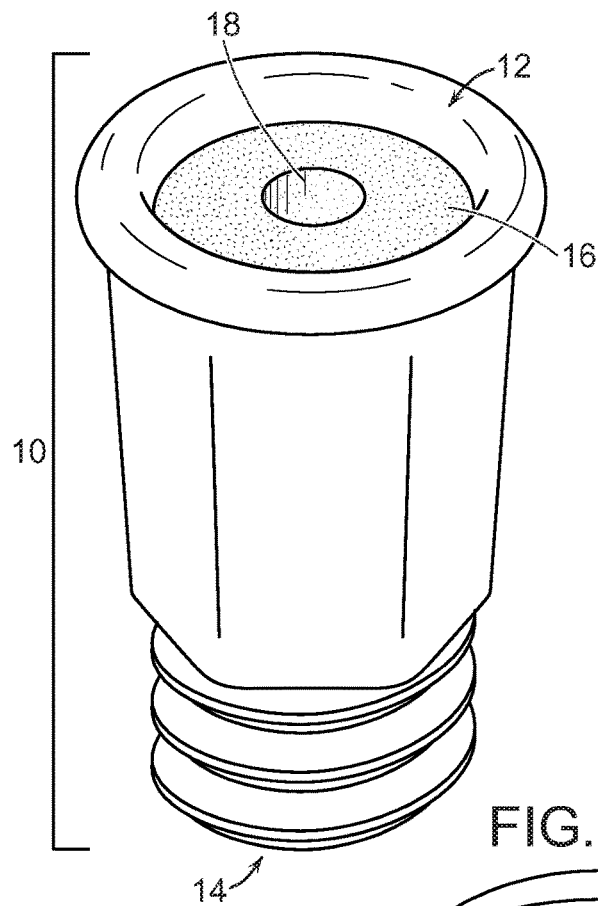
FIG. 1 shows (A) an unsealed, (B) sealed and (C) closed bottom of the sanitizing device of the present invention.

The present invention will now be described in detail in reference to the figures.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the sanitizing device" includes one or more embodiments, which are described herein and/or which will become apparent to those ordinarily skilled in the art upon reading the disclosure.

The present invention relates to a method for sanitizing a medical injection port for coupling to an injection device. The method comprises providing a sanitizing device. The sanitizing device is designed to be removably coupled to an injection device. In a preferred embodiment, the sanitizing device of the present invention is packaged coupled to the injection device. An injection device is any device used by medical personnel to administer an injectable substance into a subject. The injection device may be, for example, a syringe or catheter tubing or other device known in the art. The injection device may be a device used for intravenous, intramuscular or subcutaneous injection. In the context of the present invention, the term "injection device" may refer to devices suitable for the injection or withdrawal of fluids or other substances into or out of a body. "Sanitizing," as defined herein, is the act of applying sanitizing agents (e.g., antimicrobial agents) to the surface of non-living objects (e.g., injection ports) to destroy microorganisms that are living on the object surface. Sanitizing does not necessarily kill all microorganisms and it is less effective than sterilization but is suitable to situations where efficiency is needed and absolute sterilization is not needed or is difficult or impossible to perform.

The sanitizing device of the present invention comprises a closed first end having a fitting suitable for coupling to the injection device. The fitting may be a screw fitting, a luer lock fitting, a push-on friction fitting, or other fitting known to one of ordinary skill in the art that is suitable for coupling to an injection device. The first end of the sanitizing device of the present invention is sized to fit the end of the injection device.

The sanitizing device of the present invention further comprises a second end that comprises a recess containing an absorbent material substantially saturated with a sanitizing agent. The second end of the sanitizing device is sized to accept an injection port for sanitizing. The second end of the sanitizing device is sealed with a removable seal to prevent evaporation of the sanitizing agent prior to use. The removable seal is substantially resistant or completely resistant to moisture permeability. The absorbent material can be selected from one or more of the group consisting of open cell foam, woven material and non-woven material or other suitable material. The material is compressible and expandable (e.g., pliable) such that when an injection port is inserted into the sanitizing device, the material allows the entry of the injection port into the sanitizing device by compressing and then expands to fill the voids between the absorbent material and the injection port. Thus, the material may expand to ensure that the sanitizing fluid makes contact with the injection port during the sanitizing procedure.

The sanitizing device of the present invention, exclusive of the absorbent material, may be made of any suitable material. The material chosen is non-limiting. Plastics are preferred for the device including, but not limited to, polypropylene (PP), polyvinylchloride (PVC), polyethylene (PE) and polystyrene (PS).

In one aspect, the injection port sanitizing method of the present invention comprises removing the seal from the second end of the sanitizing device, inserting the injection port into the recess of the sanitizing device such that the absorbent material substantially saturated with a sanitizing agent substantially contacts the injection port, wherein the sanitizing device is contacted with the injection port for a length of time such that the injection port is sanitized. The sanitizing procedure of the present invention is typically performed for a time selected from the group consisting of at least five seconds, at least twenty seconds and at least sixty seconds. The sanitizing procedure of the present invention is typically performed for a time selected from a group consisting of up to approximately fifteen seconds, up to approximately thirty seconds, up to approximately sixty seconds, up to approximately 120 seconds and up to approximately 300 seconds.

During sanitizing, the user may move the sanitizing device on the injection port by, for example, rotating the sanitizing device and injection port and/or moving the injection port in and out of or partially in and out of the sanitizing device. These motions help to ensure that the sanitizing solution reaches all of the surfaces of the injection port. The injection port is then removed from the sanitizing device and the sanitizing device is removed from the injection device and the injection device coupled to the injection port. The injection device may be a syringe or a catheter port or other device known to one of ordinary skill in the art.

Sanitizing solutions that may be used with the device and method of the present invention include, but are not limited to, one or more of isopropyl alcohol and chlorhexidine or other sanitizing agent known to one of ordinary skill in the art. In a one aspect, the sanitizing agent is isopropyl alcohol at a concentration of approximately 60% to approximately 80%, approximately 65% to approximately 75%, approximately 70% or 70%±1%.

The patient or subject for which the injection port is inserted may be any animal, particularly any mammal and, more particularly, a human.

The sanitizing device of the present invention will now be described in view of the figures.

Figure 1B:
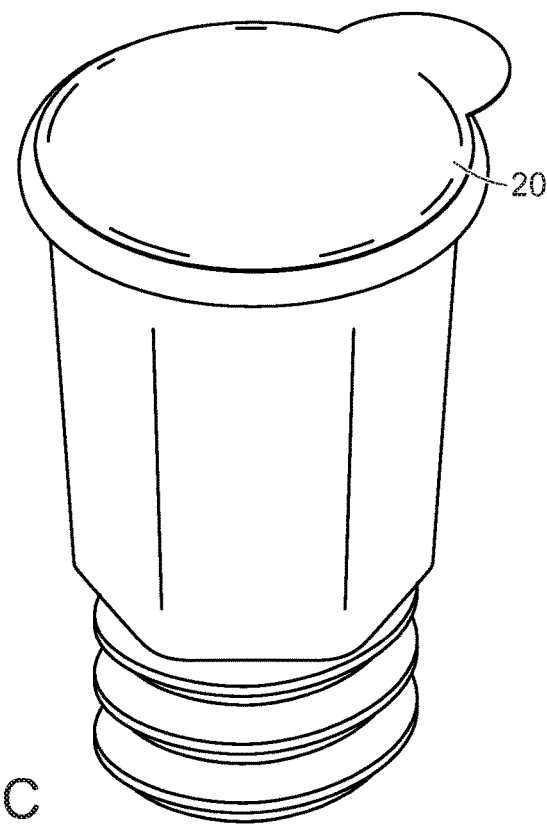
Figure 1C:
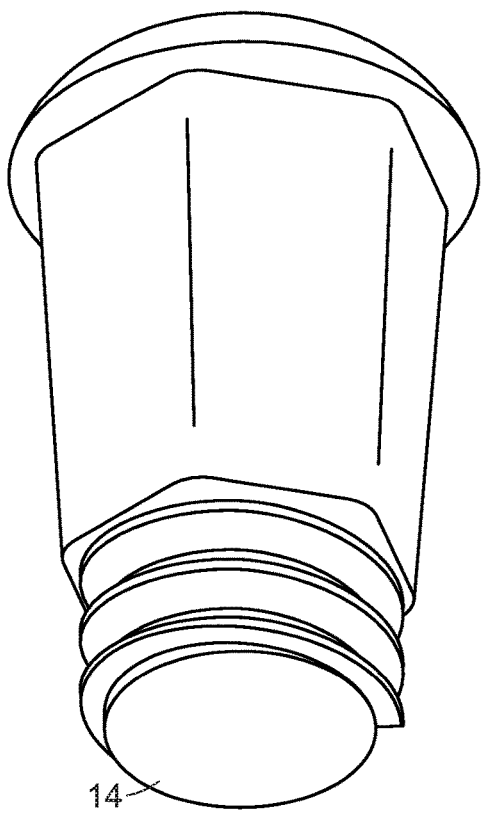

FIG. 1A shows an embodiment of the sanitizing device 10 of the present invention. The device has an open second end 12 and a closed first end 14. In the recess of the opened second end 12 of the device 10 is absorbent material 16 substantially saturated with a sanitizing agent. In an embodiment, the absorbent material may have a recess or open area 18 in the center for easier insertion of an injection port, when used. Alternatively, the absorbent material may be made of multiple pieces of absorbent material extending from the bottom of the recess to the opening, the multiple pieces being repositioned (i.e., moved or pushed aside) when an injection port is inserted. The absorbent material may be held in place with an adhesive, if desired. FIG. 1B shows the seal 20 on the sanitation device to be removed prior to use. FIG. 1O shows the closed end 14 of the sanitizing device.

Figure 2A:
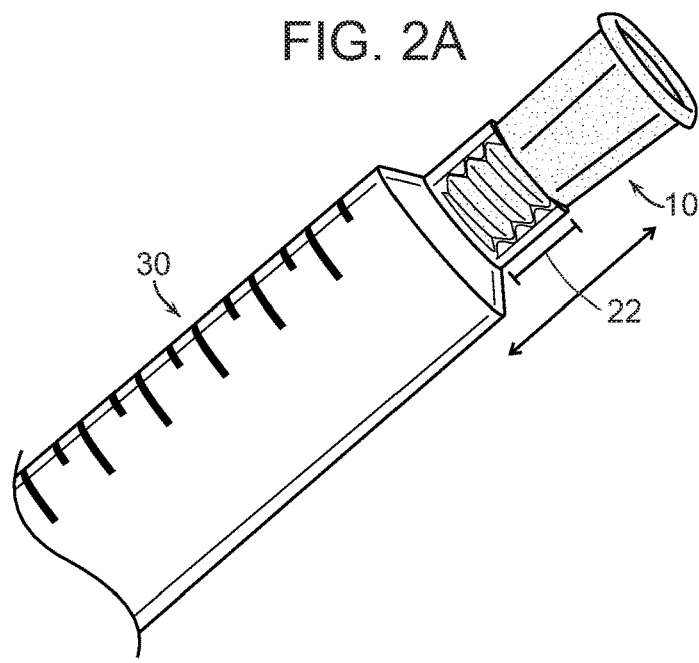
FIG. 2 shows the sanitizing device of the present invention with (A) a screw fitting, (B) a push-on fitting and (C) a luer lock fitting.
Figure 2B:
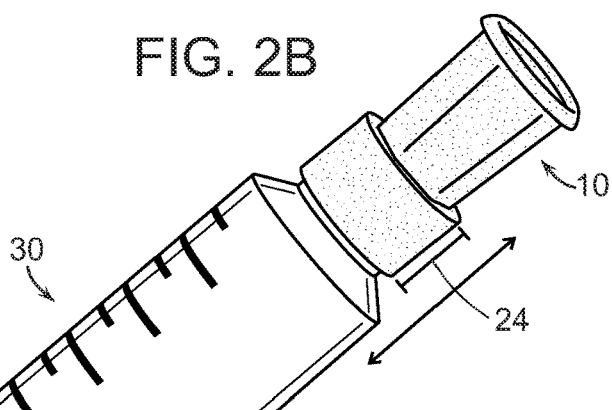
Figure 2C:
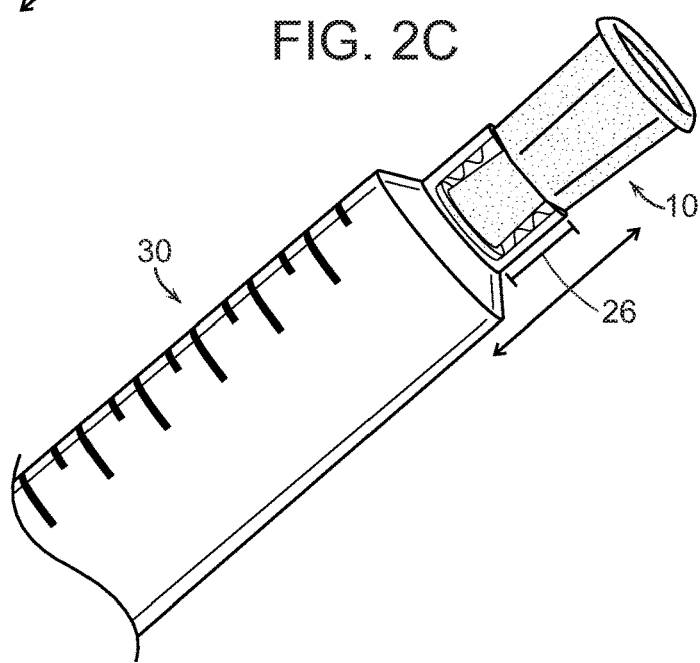

FIGS. 2A-C show three variations of the sanitation device 10 removably attached to an injection device, in this case a syringe 30. FIG. 2A shows a screw fitting 22, FIG. 2B shows a friction fit fitting 24 and FIG. 2C shows a Luer lock fitting 26. The arrows indicate that the sanitizing device is removable from the injection device.

Figure 3:
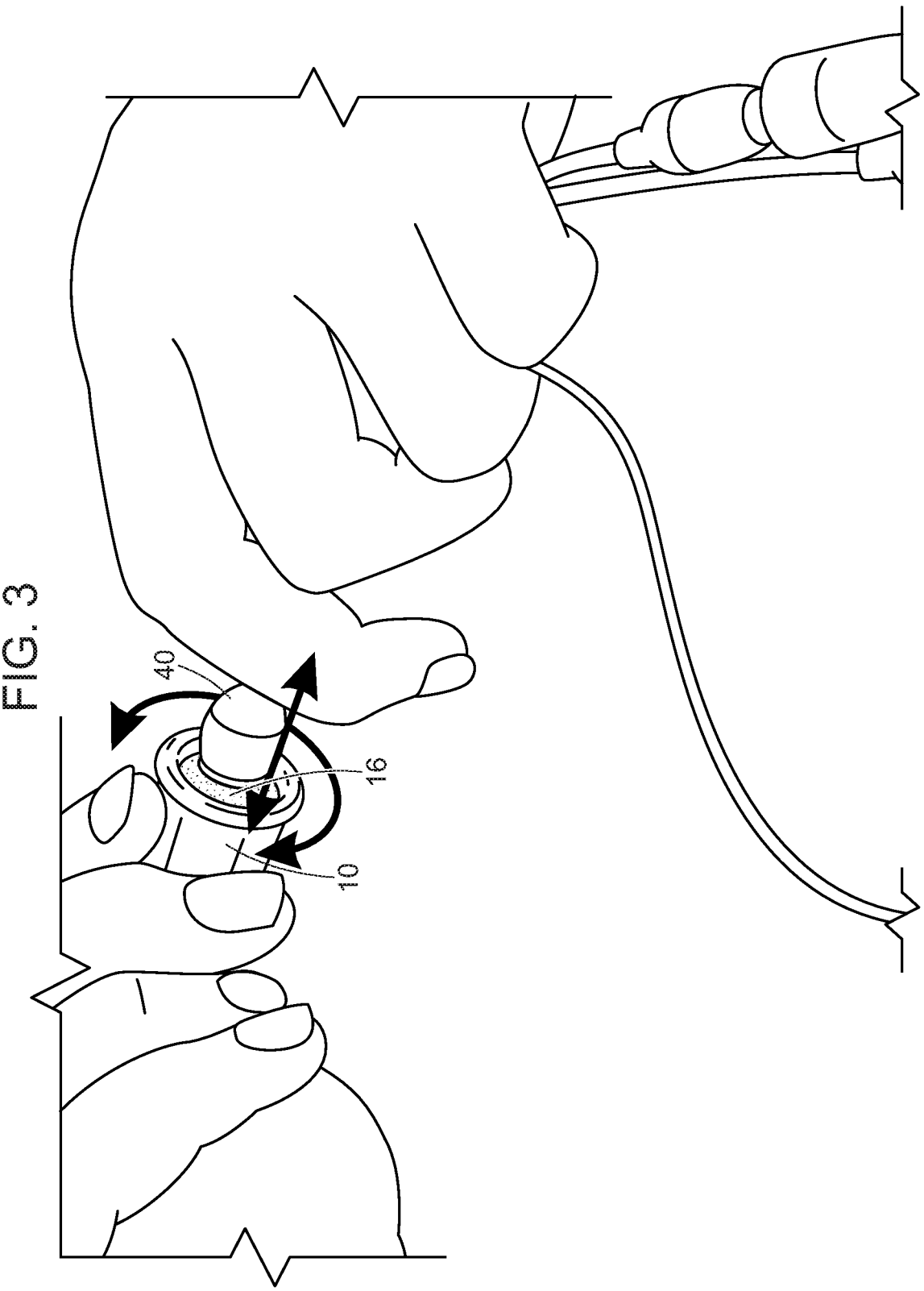
FIG. 3 shows the sanitizing device being used to sanitize an injection port.

FIG. 3 shows the sanitizing device 10 in use. The injection port 40, is shown inserted into the absorbent material substantially saturated with a sanitizing agent 16. The arrows indicate motions used by a user when sanitizing the injection port with the sanitizing device of the present invention.

FIG. 4 shows a side view of an alternate design of the sanitization device 10 of the present invention. The first end of the device 14 is flared 44 for easier manipulation by a user. The body of the device comprises a number of ridges 42 for easier gripping of the device by a user.

FIG. 5 shows a cross-sectional view of the sanitization device 10 of the present invention attached to an injection device 30. It can be seen that the flare 44 abuts the injection device allowing for easier user manipulation of the device during removal of the sanitizing device from the injection device by using the fingers of the hand holding the injection device. Further, the ridges 42 allow for easier removal of the sanitizing device if the user is using the hand that is not holding the injection device. The absorbent material 16 is shown in end 12. The removable seal 20 is not shown. A barrier 46 between the open second end and attachment first end is shown. Thus, in this alternate design, the first end is closed at its base.

Figure 6:
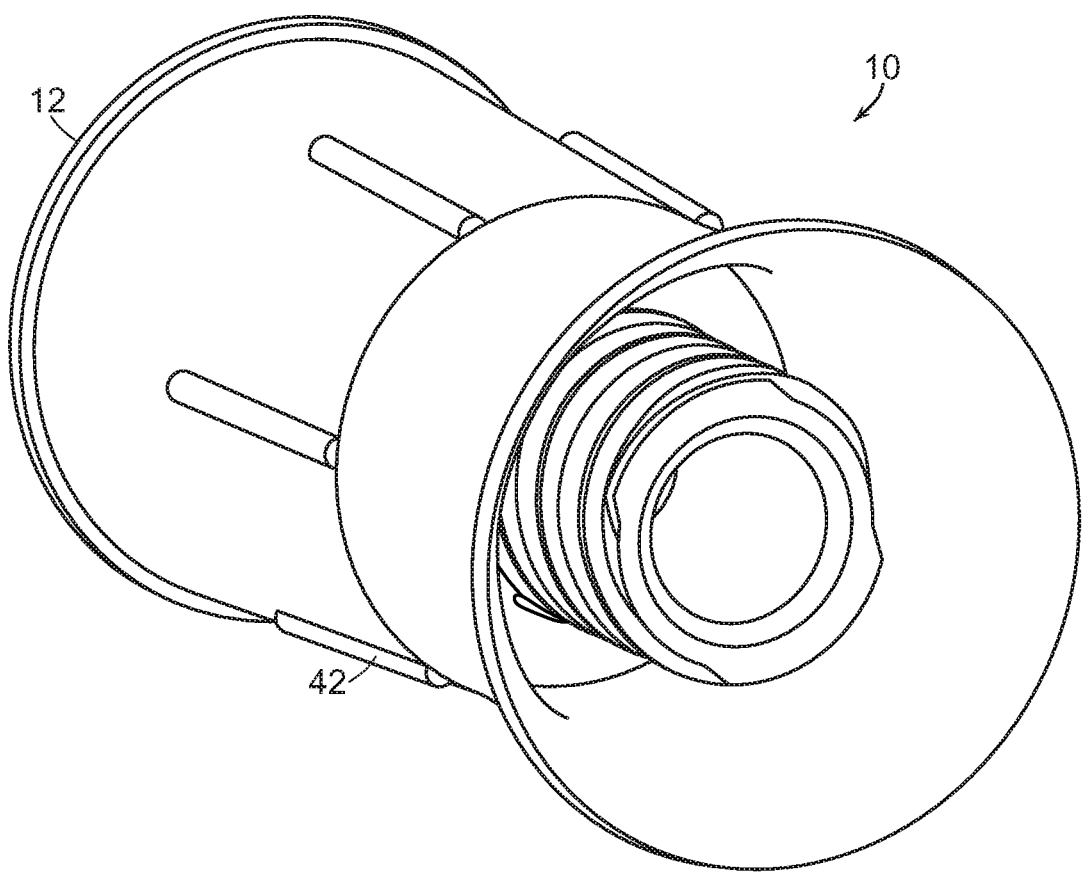
FIG. 6 shows a perspective view of the alternate design of the sanitization device of the present invention.

FIG. 6 shows a perspective view of the alternate design of the sanitization device 10 of the present invention.

The terms "about" and "approximately" include the recited number and ±5% or ±2%, depending on context.

Any series or range of numbers is inclusive of all values in the series or range even if any particular value is not explicitly stated.

Variations, modifications, and other implementations of what is described herein will occur to those of ordinary skill in the art without departing from the spirit and the scope of the invention as claimed. Accordingly, the invention is to be defined not by the preceding illustrative description, but instead by the spirit and scope of the following claims.

I claim:

1. A method for sanitizing a medical injection port for coupling to a syringe, comprising:
   a) providing, a sanitizing device removably coupled to a female screw fitting of an injection end of the syringe, said sanitizing device having a single unitary structure comprising:
      i) a closed first end having a male engagement element removably engaging the female screw fitting of the syringe,
      ii) a second end comprising a recess formed in the single unitary structure, the second end sealed with a removable seal, wherein the second end is configured without a threaded portion on an interior surface of the recess of the single unitary structure, and
      iii) an absorbent material contained within the recess of the second end, the absorbent material configured to contact the interior surface of the recess of the single unitary structure, the absorbent material being substantially saturated with a sanitizing agent, the absorbent material comprising a recess through a center thereof, the recess of the absorbent material configured to enable insertion of the medical injection port into the absorbent material;
   b) removing the removable seal from the second end of the sanitizing device;
   c) inserting the medical injection port into the recess of the sanitizing device such that the absorbent material substantially saturated with the sanitizing agent contacts the medical injection port;
   d) moving the sanitizing device on the medical injection port to facilitate the absorbent material scrubbing and sanitizing the medical injection port under conditions appropriate for preventing bloodstream inventions;
   e) removing the sanitizing device from the medical injection port and the syringe; and
   f) coupling the medical injection port to the syringe after removing the sanitizing device from the medical injection port and the syringe.

2. The method of claim 1, wherein said removable seal is substantially resistant to moisture permeability.

3. The method of claim 1, wherein said sanitizing agent is selected from the group consisting of isopropyl alcohol and chlorhexidine.

4. The method of claim 3, wherein said sanitizing agent is isopropyl alcohol at a concentration of approximately 65% to 75%.

5. The method of claim 1, wherein said absorbent material is selected from the group consisting of an open cell foam, a woven material, and a non-woven material.

6. The method of claim 1, wherein the sanitizing device is moved on the medical injection port for a length of time selected from the group consisting of at least five seconds, at least twenty seconds, and at least sixty seconds.

7. The method of claim 1, wherein said medical injection port is suitable for injection to sites selected from the group consisting of intravenous, intramuscular, and subcutaneous injection sites.

8. A device for performing active scrubbing of a medical injection port, said device comprising:
 a syringe for administering or withdrawing fluid into or out of a subject via the medical injection port; and
 a sanitizing device having a single unitary structure comprising:
  a closed first end having a male engagement element suitable for engaging with a female screw fitting of an injection end of the syringe,
  a second end comprising a recess formed in the single unitary structure, the second end sealed with a removable seal, wherein the second end is configured without a threaded portion on an interior surface of the recess of the single unitary structure, and
  an absorbent material contained within the recess of the second end, the absorbent material configured to contact the interior surface of the recess of the single unitary structure, the absorbent material being substantially saturated with a sanitizing agent, the absorbent material comprising a recess through a center thereof, the recess of the absorbent material configured to enable insertion of the medical injection port into the absorbent material.

9. The device of claim 8, wherein said removable seal is substantially resistant to moisture permeability.

10. The device of claim 8, wherein said sanitizing agent is selected from the group consisting of isopropyl alcohol and chlorhexidine.

11. The device of claim 10, wherein said sanitizing agent is isopropyl alcohol at a concentration of approximately 65% to 75%.

12. The device of claim 8, wherein said absorbent material is selected from the group consisting of an open cell foam, a woven material, and a non-woven material.

13. A sanitizing device for performing active scrubbing of a medical injection port, said sanitizing device having a single unitary structure comprising:
 a closed first end having a male engagement element suitable for engaging with a female screw fitting of an injection end of a syringe;
 a second end comprising a recess formed in the single unitary structure, the second end sealed with a removable seal, wherein the second end is configured without a threaded portion on an interior surface of the recess of the single unitary structure; and
 an absorbent material contained within the recess of the second end, the absorbent material configured to contact the interior surface of the recess of the single unitary structure, the absorbent material being substantially saturated with a sanitizing agent, the absorbent material comprising a recess through a center thereof, the recess of the absorbent material configured to enable insertion of the medical injection port into the absorbent material.

14. The sanitizing device of claim 13, wherein said removable seal is substantially resistant to moisture permeability.

15. The sanitizing device of claim 13, wherein said sanitizing agent is selected from the group consisting of isopropyl alcohol and chlorhexidine.

16. The sanitizing device of claim 15, wherein said sanitizing agent is isopropyl alcohol at a concentration of approximately 65% to 75%.

17. The sanitizing device of claim 13, wherein said absorbent material is selected from the group consisting of an open cell foam, a woven material, and a non-woven material.

18. The device of claim 8, wherein the male engagement element is either a screw fitting or a luer lock fitting.

19. The sanitizing device of claim 13, wherein the male engagement element is either a screw fitting or a luer lock fitting.

* * * * *